(12) United States Patent
Greene

(10) Patent No.: US 11,904,063 B2
(45) Date of Patent: Feb. 20, 2024

(54) DISINFECTING GLOVE SYSTEM

(71) Applicant: Corrida Marie Greene, Moncks Corner, SC (US)

(72) Inventor: Corrida Marie Greene, Moncks Corner, SC (US)

(*) Notice: Subject to any disclaimer, the term of this patent is extended or adjusted under 35 U.S.C. 154(b) by 81 days.

(21) Appl. No.: 17/400,610

(22) Filed: Aug. 12, 2021

(65) Prior Publication Data

US 2022/0047748 A1 Feb. 17, 2022

Related U.S. Application Data

(60) Provisional application No. 63/066,168, filed on Aug. 15, 2020.

(51) Int. Cl.
| | |
|---|---|
| *A61L 2/18* | (2006.01) |
| *A47L 13/19* | (2006.01) |
| *A01N 33/12* | (2006.01) |
| *B08B 1/00* | (2006.01) |

(52) U.S. Cl.
CPC ............... *A61L 2/18* (2013.01); *A01N 33/12* (2013.01); *A47L 13/19* (2013.01); *B08B 1/006* (2013.01); *A61L 2202/17* (2013.01)

(58) Field of Classification Search
None
See application file for complete search history.

(56) References Cited

U.S. PATENT DOCUMENTS

| | | |
|---|---|---|
| 4,853,978 A | 8/1989 | Stockum |
| 5,003,638 A | 4/1991 | Miyake et al. |
| 5,187,815 A | 2/1993 | Stern et al. |
| 5,644,813 A | 7/1997 | Puskas |
| 5,956,770 A | 9/1999 | Dennis |
| 6,098,234 A | 8/2000 | Jackson |
| 6,370,694 B1 | 4/2002 | Michelson |
| 6,393,614 B1 | 5/2002 | Eichelbaum |
| 6,550,092 B1 | 4/2003 | Brown et al. |
| 6,673,404 B1 | 1/2004 | Yeh et al. |
| 6,913,758 B2 | 7/2005 | Hourihan et al. |
| 7,033,100 B2 | 4/2006 | Barton et al. |
| 7,108,440 B1* | 9/2006 | Gruenbacher .......... A47L 13/19 401/133 |
| 7,210,171 B2 | 5/2007 | Jacobs et al. |
| 7,584,519 B2 | 9/2009 | Ouellette et al. |

(Continued)

FOREIGN PATENT DOCUMENTS

GB 2382018 A * 5/2003 ............. A47L 13/18

*Primary Examiner* — Holly Kipouros

(74) *Attorney, Agent, or Firm* — Olav M. Underdal; IDP Patent Services

(57) ABSTRACT

A disinfecting glove includes: a glove body that can be made of nitril rubber; a disinfecting pad that includes a pad body with a disinfecting agent applied and optionally an adhesive layer, a scrubbing portion, a cleaning portion, and dusting portions, such that the disinfecting pad can be detachably or permanently positioned on a palmar side of the glove body, such that the disinfecting glove can be used to clean and disinfect a surface. Also disclosed is a disinfecting glove system including a pair of glove assemblies, each including a glove container and a disinfecting glove; and a disinfecting system including a plurality of pairs of disinfecting gloves; and a plurality of disinfecting shoe covers, each including a shove cover body and a disinfecting pad.

10 Claims, 9 Drawing Sheets

(56) References Cited

U.S. PATENT DOCUMENTS

| | | | |
|---|---|---|---|
| 7,624,468 | B2 | 12/2009 | Reddy et al. |
| 7,874,020 | B1 | 1/2011 | Franklin |
| 8,578,548 | B1 | 11/2013 | Costello et al. |
| 9,038,819 | B2 | 5/2015 | Perelli |
| 9,771,201 | B2 | 9/2017 | Yao et al. |
| 10,028,640 | B2 | 7/2018 | McGrath |
| 10,117,558 | B1 * | 11/2018 | Restrepo ............ A41D 19/0024 |
| 2006/0272116 | A1 | 12/2006 | Thompson |
| 2007/0067932 | A1 | 3/2007 | Young et al. |
| 2007/0104766 | A1 | 5/2007 | Wang et al. |
| 2007/0192975 | A1 | 8/2007 | Aseff |
| 2008/0244848 | A1 * | 10/2008 | Firouzman .............. A47L 13/12 |
| | | | 15/118 |
| 2009/0241237 | A1 | 10/2009 | Greenfield |
| 2010/0218326 | A1 | 9/2010 | Yamaguchi |
| 2011/0125093 | A1 | 5/2011 | Tan |
| 2014/0289987 | A1 * | 10/2014 | Filho ....................... A47L 13/18 |
| | | | 15/227 |
| 2015/0135401 | A1 | 5/2015 | Husain |
| 2016/0113472 | A1 * | 4/2016 | Redd ....................... A47L 13/12 |
| | | | 15/118 |
| 2016/0324227 | A1 | 11/2016 | Bowen et al. |
| 2017/0143178 | A1 | 5/2017 | Mesiti |
| 2018/0214586 | A1 | 8/2018 | Louis et al. |
| 2021/0085002 | A1 | 3/2021 | Smith |

\* cited by examiner

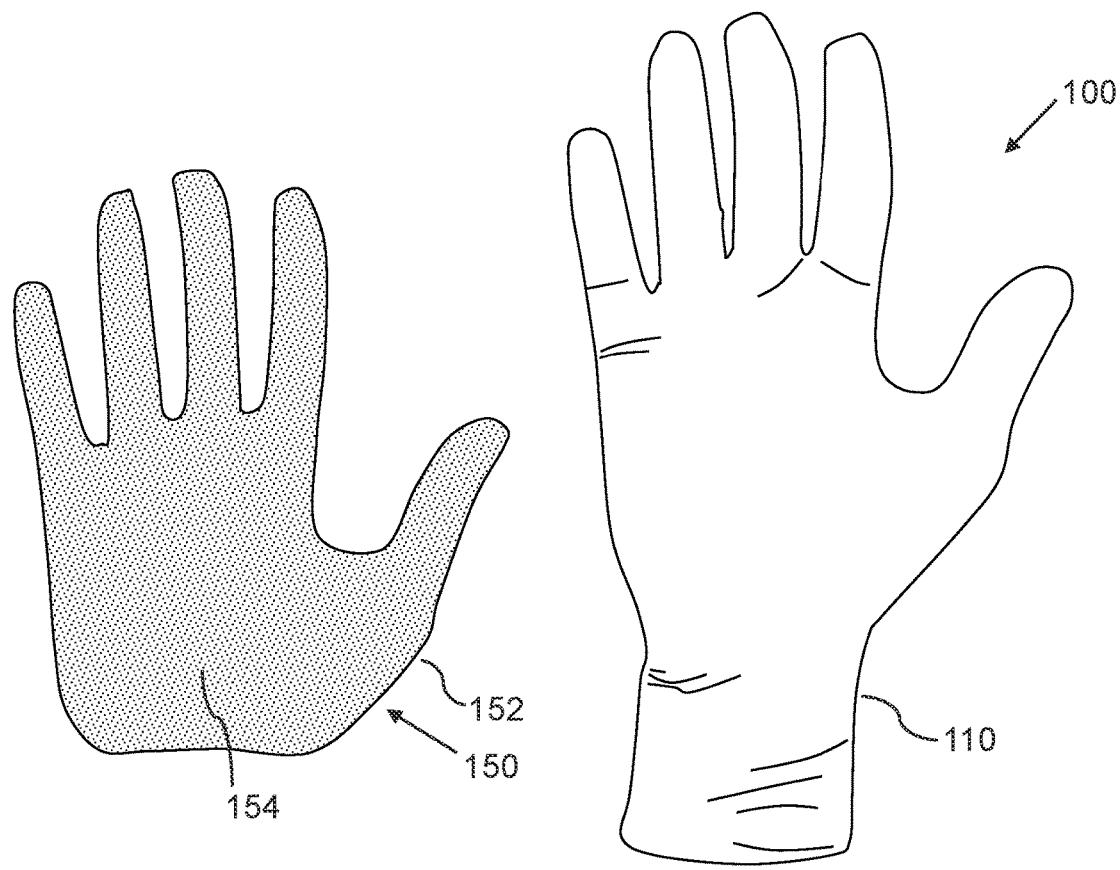

FIG. 5
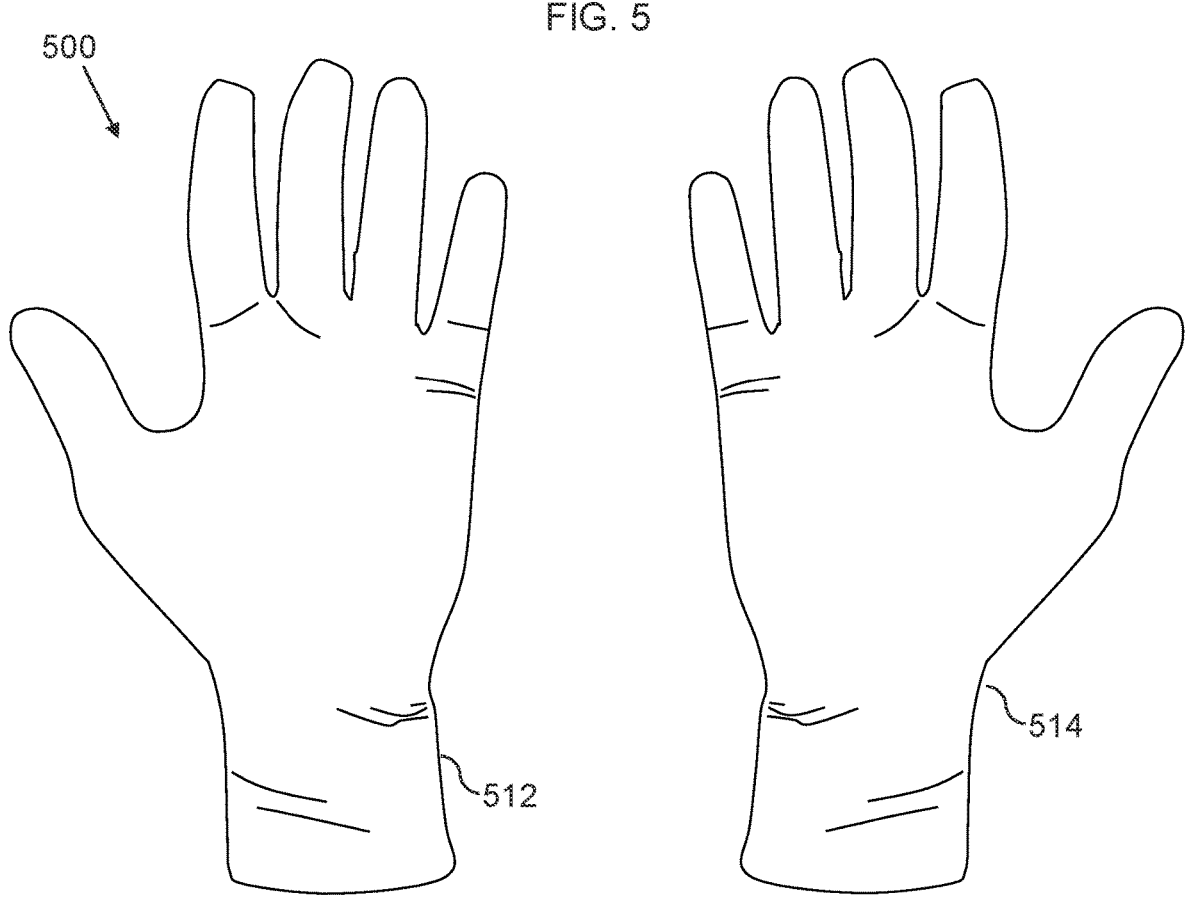
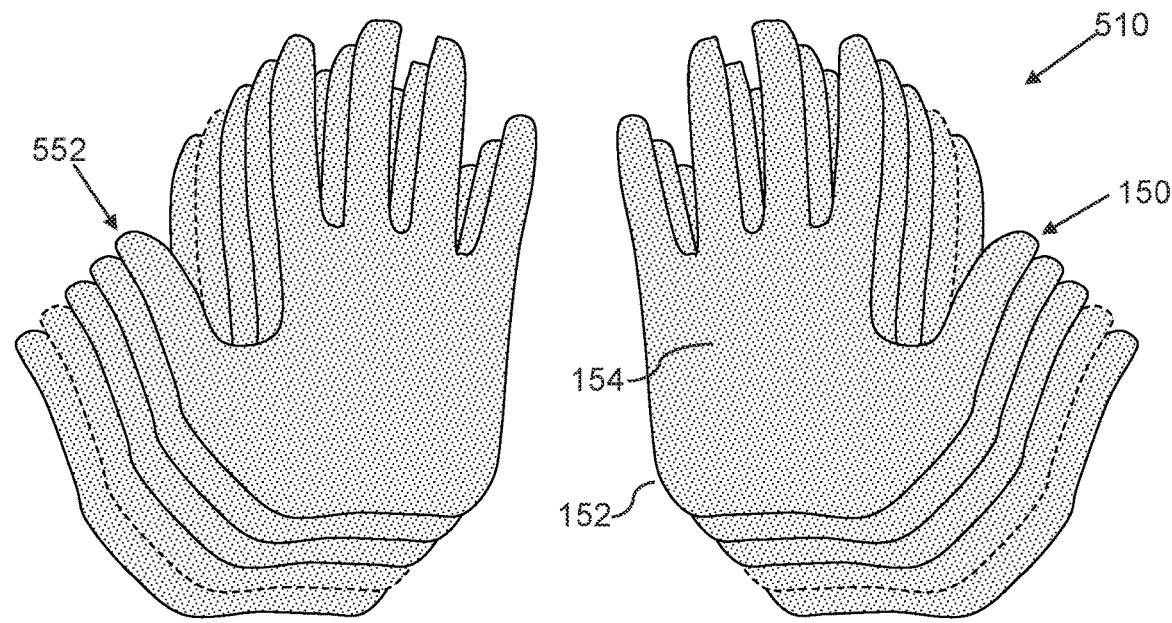

DISINFECTING GLOVE SYSTEM

CROSS-REFERENCE TO RELATED APPLICATIONS

This application claims the benefit of U.S. Provisional Application No. 63/066,168, filed Aug. 15, 2020; which is hereby incorporated herein by reference in its entirety.

FIELD OF THE INVENTION

The present invention relates generally to the field of disposable and reusable gloves, and more particularly to methods and systems for disposable and reusable disinfecting gloves for use as personal protective equipment.

BACKGROUND OF THE INVENTION

It is desirable for consumers to easily disinfect and sanitize items that are purchased in retail stores, grocery stores, etc. in a fast and hassle-free manner, in order to protect themselves and loved ones from potentially deadly viruses, germs, and bacteria that could be brought into the home on the surfaces of contaminated items purchased.

It is also desirable for healthy consumers that encounter items that could have been exposed to bacteria, germs, and viruses by infected consumers to not be contaminated or otherwise affected by exposure to the germs. Some consumers do not even have the dexterity required to properly utilize current solutions in order to fully disinfect items they purchase for use.

Other consumers are prevented from coming directly into contact with disinfecting fluids and certain types of gloves due to allergies. Currently, there exists no easy way to safely protect hands and conveniently disinfect products purchased in retail locations or online and brought into homes or community settings for use.

Current solutions to disinfecting the exterior or packaging of items purchased for consumer use provide highly unsatisfactory performance. They are hard to use and the consumer potentially spreads germs on the surface of the item, when holding the item with one hand while attempting to sanitize the item by using a disinfecting solution in the other hand; which is an awkward process that requires high consumer effort, and unnecessarily wastes time. Other personal protective equipment solutions can be worn on the hands to protect them from germs, bacteria, and viruses; however, the material protecting the hand comes into contact with potential germs, bacteria, and viruses on the surface of objects to be cleaned, and can thereby transfer germs around the objects, as well as onto any other items touched by the consumer.

As such, considering the foregoing, it may be appreciated that there continues to be a need for novel and improved devices and methods for personal protective equipment that fulfill those needs and addresses the aforementioned deficiencies by providing a quick, easy, and effective way for consumers to disinfect items they come into contact with and prevent the spread of bacteria and germs.

SUMMARY OF THE INVENTION

The foregoing needs are met, to a great extent, by the present invention, wherein in aspects of this invention, enhancements are provided to the existing model of gloves for use as personal protective equipment.

In an aspect, a disinfecting glove can include:
a) a glove body, which can be made of rubber, including nitrile rubber, or latex; and
b) a disinfecting pad, which can be detachably positioned on a palmar side of the glove body, such that the disinfecting pad can be saturated with:
   i. a disinfecting agent;
such that the disinfecting glove can be used to clean a surface, such that the disinfecting pad wipes the surface and applies the disinfecting agent to the surface.

In a related aspect, a disinfecting pad can include:
a) a pad body, which further includes the disinfecting agent; and
b) an adhesive layer, which is positioned on a portion of a palmar side of the pad body;
such that the adhesive layer can be configured to attach the disinfecting pad to a palmar side of the at least one glove body, such that the adhesive layer is between the pad body and the at least one glove body.

In a related embodiment, the pad body can be made from:
a) a polypropylene fabric;
b) a microfiber fabric, which for example can be made from polyesters; polyamides; and combinations of polyester, polyamide, and polypropylene;
c) a cotton fabric; or
d) combinations thereof.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 2B is an exploded view of parts of a disinfecting glove, according to an embodiment of the invention.

FIG. 2C is a bottom view of a disinfecting pad, according to an embodiment of the invention.

FIG. 2D is a schematic cross-sectional view of a disinfecting glove taken along section line 2D-2D of FIG. 2A, according to an embodiment of the invention.

FIG. 5 is a perspective view of a disinfecting glove system, according to an embodiment of the invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Figure 1A:
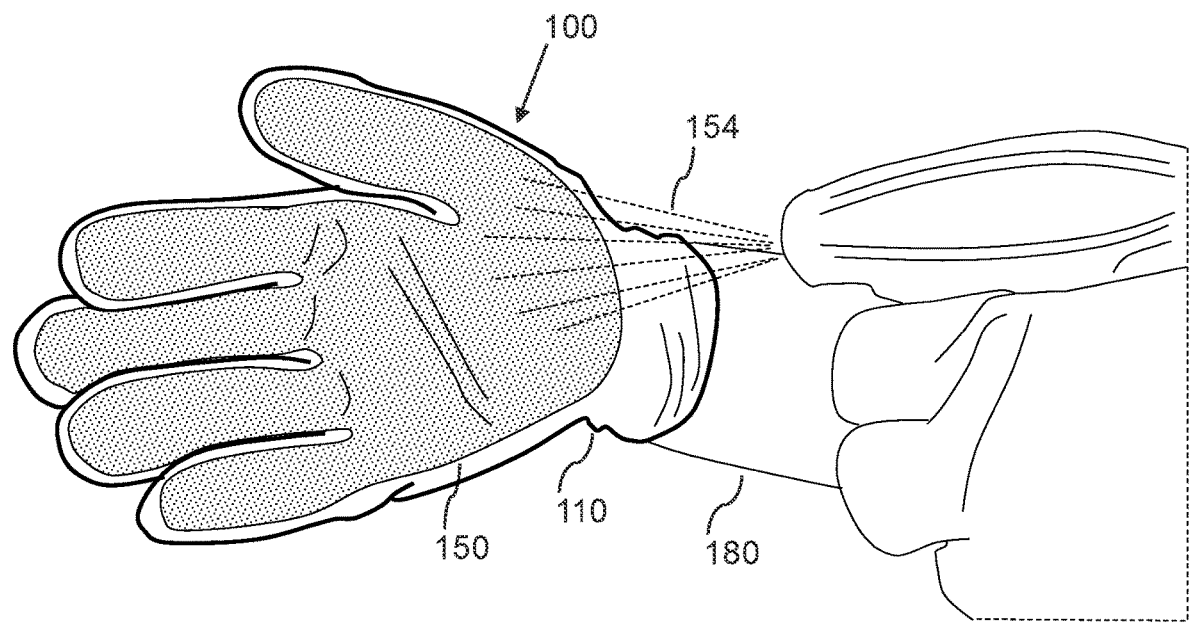
FIG. 1A is a perspective view of a disinfecting glove in use, wherein a user is applying a disinfecting agent to a disinfecting pad of the disinfecting glove, according to an embodiment of the invention.
Figure 1B:
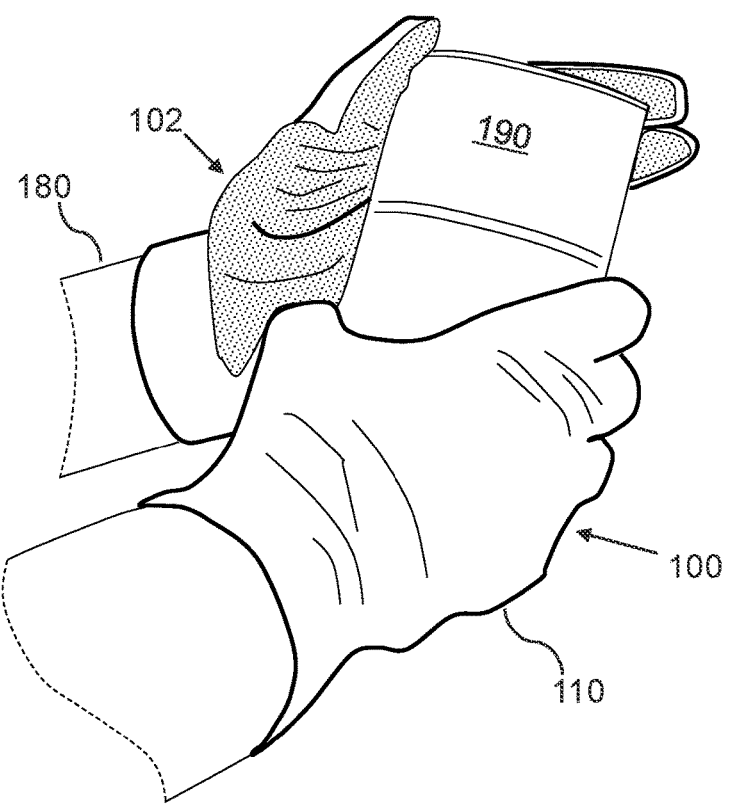
FIG. 1B is a perspective view of a pair disinfecting gloves in use, according to an embodiment of the invention.
Figure 2A:
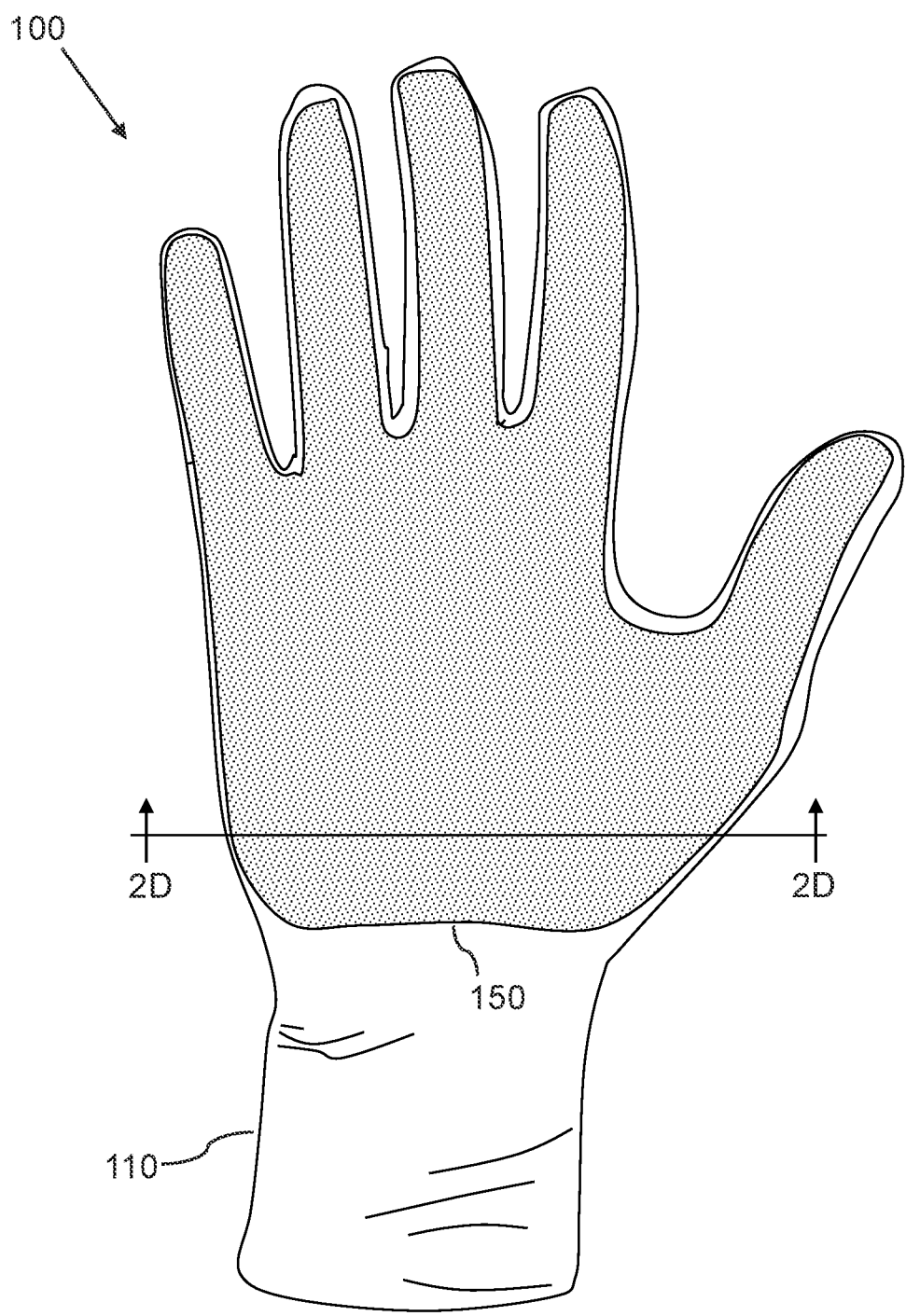
FIG. 2A is a bottom view of a disinfecting glove, showing a palmar side of the disinfecting glove, according to an embodiment of the invention.

In the following, we describe the structure of an embodiment of a disinfecting glove 100 with reference to FIG. 1, in such manner that like reference numerals refer to like components throughout; a convention that we shall employ for the remainder of this specification.

In an embodiment, as shown in FIGS. 1A, 1B, 2A, and 2B, a disinfecting glove 100 can include:
a) a glove body 110, which can be made of a waterproof, puncture and/or chemical resistant material, such as natural or synthetic rubber (including nitrile butadiene synthetic rubber, latex, closed-cell neoprene), PVC, or silicone; such that the glove body is configured to be worn on a hand of a user 180; and
b) a disinfecting pad 150, which can be configured to be detachably positioned on an inner side (i.e. a palmar side) of the glove body 110, such that the disinfecting pad 150 can be connected to the glove body 110 with an adhesive, a threaded/sewn connection, or other attachment mechanism/method,
wherein the disinfecting pad 150 can be configured to receive a disinfecting agent 154, such that the disinfecting pad 150 can further include (i.e. be saturated with):
i. a disinfecting agent 154, which can be configured as a disinfecting fluid, or in some related alternative embodiments can be a dry or moist powder or granulate that can be dispersed in or on the disinfecting pad 150;
such that the disinfecting glove 100 can be used to clean and disinfect a surface 190, such that the disinfecting pad wipes the surface and applies the disinfecting agent 154 to the surface.

In related embodiments, the glove body 110 can have a composite structure with an outer waterproof, puncture and/or chemical resistant coating, and inner structure or layers which may or may not be waterproof, or the glove body 110 can have a partial outer waterproof, puncture and/or chemical resistant coating, which can cover at least palmar side surfaces of the glove body 110.

In related embodiment, the disinfecting agent 154 can further include:
a) a quaternary ammonium compound, such as benzalkonium chloride;
b) Sodium hypochlorite;
c) an alcohol, such as isopropyl alcohol, ethanol, or n-propanol, and combinations thereof;
d) a phenolic, such as Chloroxylenol; and
e) combinations thereof.

In related embodiments, the disinfecting pad 150 can be pre-saturated with the disinfecting agent 154 or the disinfecting agent 154 can be applied to the disinfecting pad 150 on an inner side of the disinfecting glove 100 before use of the disinfecting glove 100, as shown in FIG. 2B, for example after purchase or cleaning of the disinfecting glove 100.

In another related embodiment, as shown in FIGS. 2B, 2C, and 2D, a disinfecting pad 150 can further include:
a) a pad body 152, which further includes the disinfecting agent 154; and
b) an adhesive layer 158, which is positioned on a portion of an inner side of the pad body, which faces the palmar side of the glove body 110;
such that the adhesive layer 158 is configured to attach the disinfecting pad to a palmar side of the at least one glove body 110, such that the adhesive layer 158 is between the pad body 152 and the at least one glove body 110.

In a related embodiment, the adhesive layer 158 can be made of a permanent adhesive (i.e., a structural adhesive), such as cyanoacrylate, such that the pad body 152 is permanently attached to the glove body 110.

In a related embodiment, the adhesive layer 158 can be made from a pressure sensitive adhesive; such as for example viscoelastic polymers made from acrylate polymer, natural or synthetic rubber (i.e., latex or synthetic thermoplastic elastomers), sticky silicone rubber or sticky silicone gel, or combinations thereof; such that the pad body 152 is detachably attached to the glove body 110.

In a related embodiment, the pad body 152 can be made from:
a) a polypropylene fabric;
b) a microfiber fabric, which for example can be made from polyesters; polyamides; and combinations of polyester, polyamide, and polypropylene;
c) a cotton fabric; or
d) combinations thereof.

Figure 3:
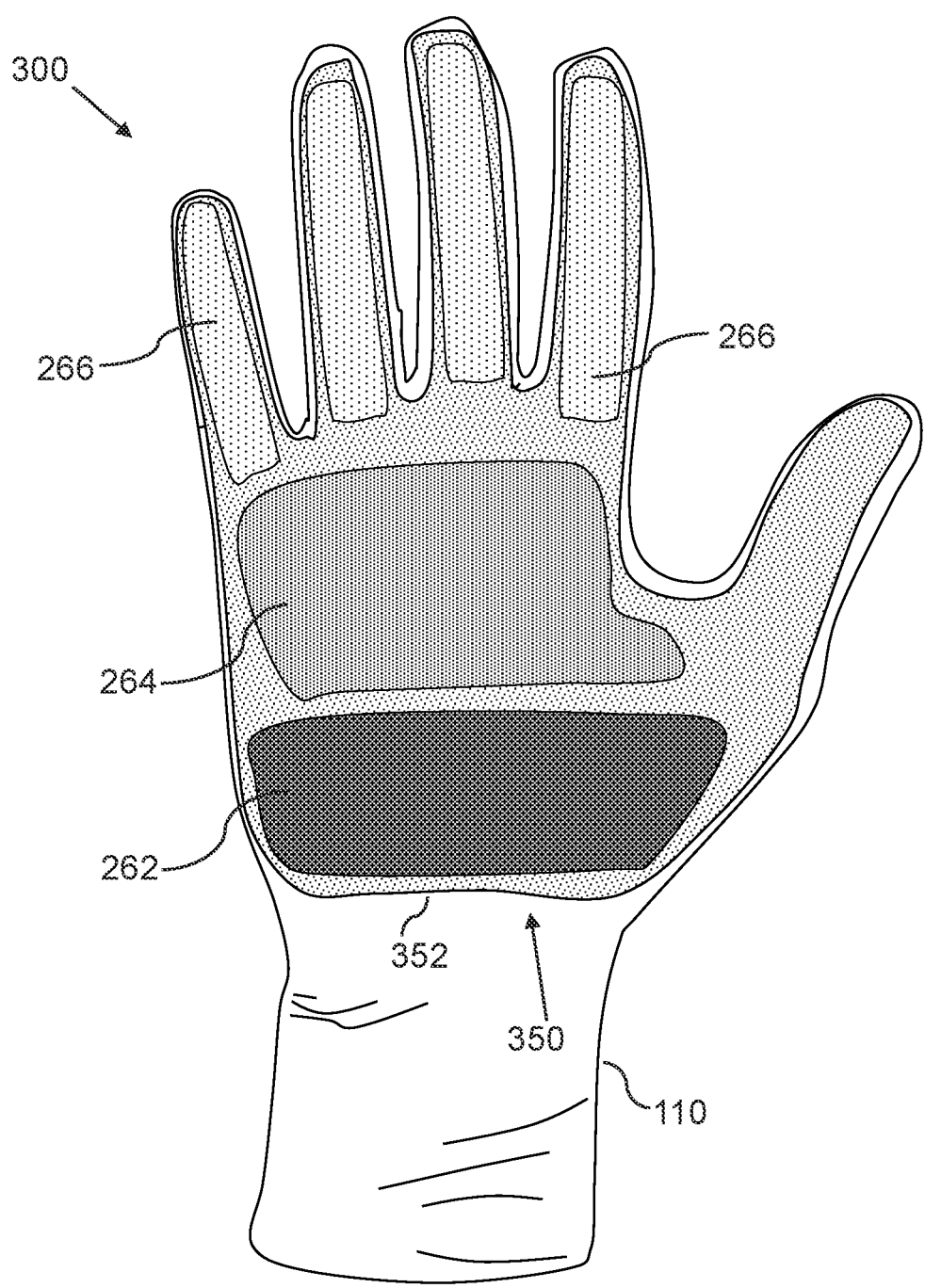
FIG. 3 is a bottom view of a disinfecting glove, showing a palmar side of the disinfecting glove, according to an embodiment of the invention.

In another related embodiment, as shown in FIG. 3, a pad body 352 of the disinfecting pad 350 of a disinfecting glove 300 can include:
a) a scrubbing portion 262, which can be positioned in a lower palm area of a palmar side of the disinfecting glove 100, wherein the scrubbing portion 262 can be configured as a scouring pad (such as SCOTCH- BRITE™ Heavy Duty Scouring Pad 86), and can for example be made of a hard plastic or metal mesh;

b) a cleaning portion 264, which can be positioned in a central palm area of the palmar side of the disinfecting glove 100 wherein the cleaning portion 264 can be configured as a cleaning cloth, which is substantially less abrasive than the scrubbing portion, and can for example be made by:
   i. a polypropylene fabric;
   ii. a microfiber fabric, which for example can be made from polyesters; polyamides; and combinations of polyester, polyamide, and polypropylene;
   iii. a cotton fabric; or
   iv. Combinations thereof; and c) dusting portions 266, which can be positioned in finger areas of the palmar side of the disinfecting glove 100, wherein the Dusting portions 266 can be configured as:
   i. tack cloths, which can for example be configured as a cotton gauze textile, which is impregnated with a tacky/sticky material, such as a petroleum-based resinous material; or
   ii. dusting cloths, which can for example be configured as soft dry microfiber cloths;

wherein the scrubbing portion 262 and the cleaning portion 264 can be saturated with a disinfecting agent 154, for scrubbing and sanitation of a surface 190; and such that the dusting portions 266 can be used for final dusting of the surface 190.

Figure 4:
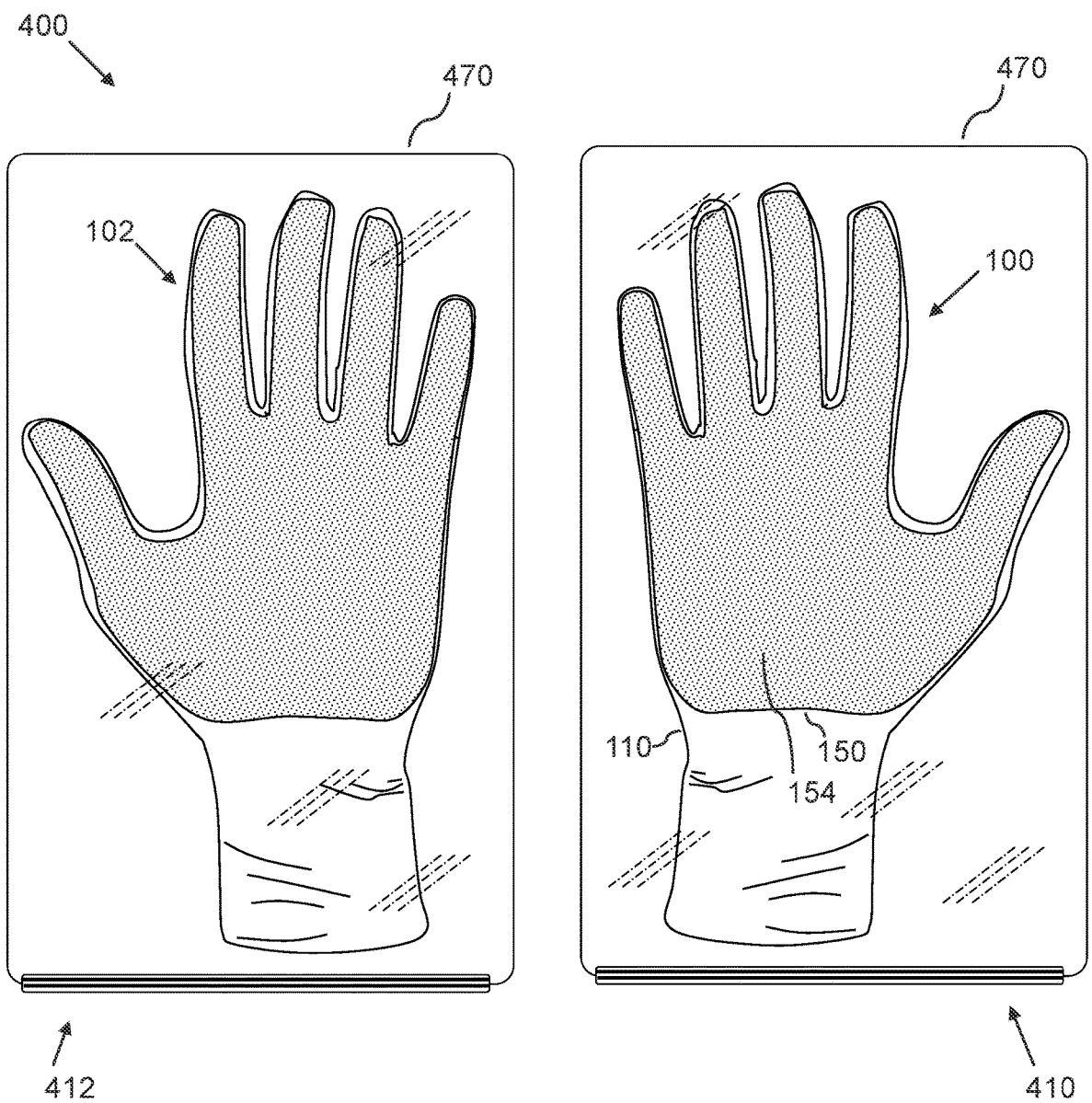
FIG. 4 is a perspective view of a disinfecting glove system, according to an embodiment of the invention.

In a related embodiment, as shown in FIG. 4, a disinfecting glove system 400, can include:

a) at least one pair of glove assemblies 410, 412, each comprising
   i. a glove container 470, which as shown can be configured as a zip lock bag; and
   ii. a disinfecting glove 100, 102, wherein a disinfecting pad 150 of the disinfecting glove 100 comprises a disinfecting agent 154;

wherein the disinfecting glove 100 is packaged and sealed inside the glove container 470, such that the disinfecting pad 150 of the disinfecting glove 100 remains saturated with disinfecting agent 154, as long as the glove container 470 remains sealed with the disinfecting glove 100 inside, such that the disinfecting pad 150 remains saturated and the disinfecting agent 154 activated until the glove assembly 410, 412 is opened for use.

In a related embodiment, as shown in FIG. 5, a disinfecting glove system 500, can include:

a) at least one pair of left and right reusable glove bodies 512, 514, which are configured for multiple-time use, such that each reusable glove body 512, 514 can be configured with a palmar material thickness (i.e. a thickness in a palm area of the glove bodies 512, 514) in a range of at least 11 mil, such as 20-40 mil, and in some cases more than 45 mil; and b) a plurality 510 of pairs of disinfecting pads 552, 150, each disinfecting pad 552, 150 including:
   i. a pad body 152, which further includes the disinfecting agent 154; and
   ii. an adhesive layer 158, which is positioned on a portion of a palmar side of the pad body;

such that the adhesive layer 158 is configured to enable the disinfecting pad 150 to be detachably positionable on a palmar side of the at least one glove body 110, such that the adhesive layer 158 is between the pad body 152 and the at least one glove body 110;

whereby the at least one glove body 110 can be reused over a prolonged period, with sequential attachment, use, and subsequent detachment and disposal of each disinfecting pad 150 in the plurality of disinfecting pads 150.

In related usage, the disinfecting glove system 500 can for example be configured with at least one reusable glove body 110 that is made of a relatively thick rubber for use in domestic or industrial kitchen, such that the disinfecting pads 150 can be configured to be one-time or limited-usage disposable disinfecting pads 150.

Figure 6:
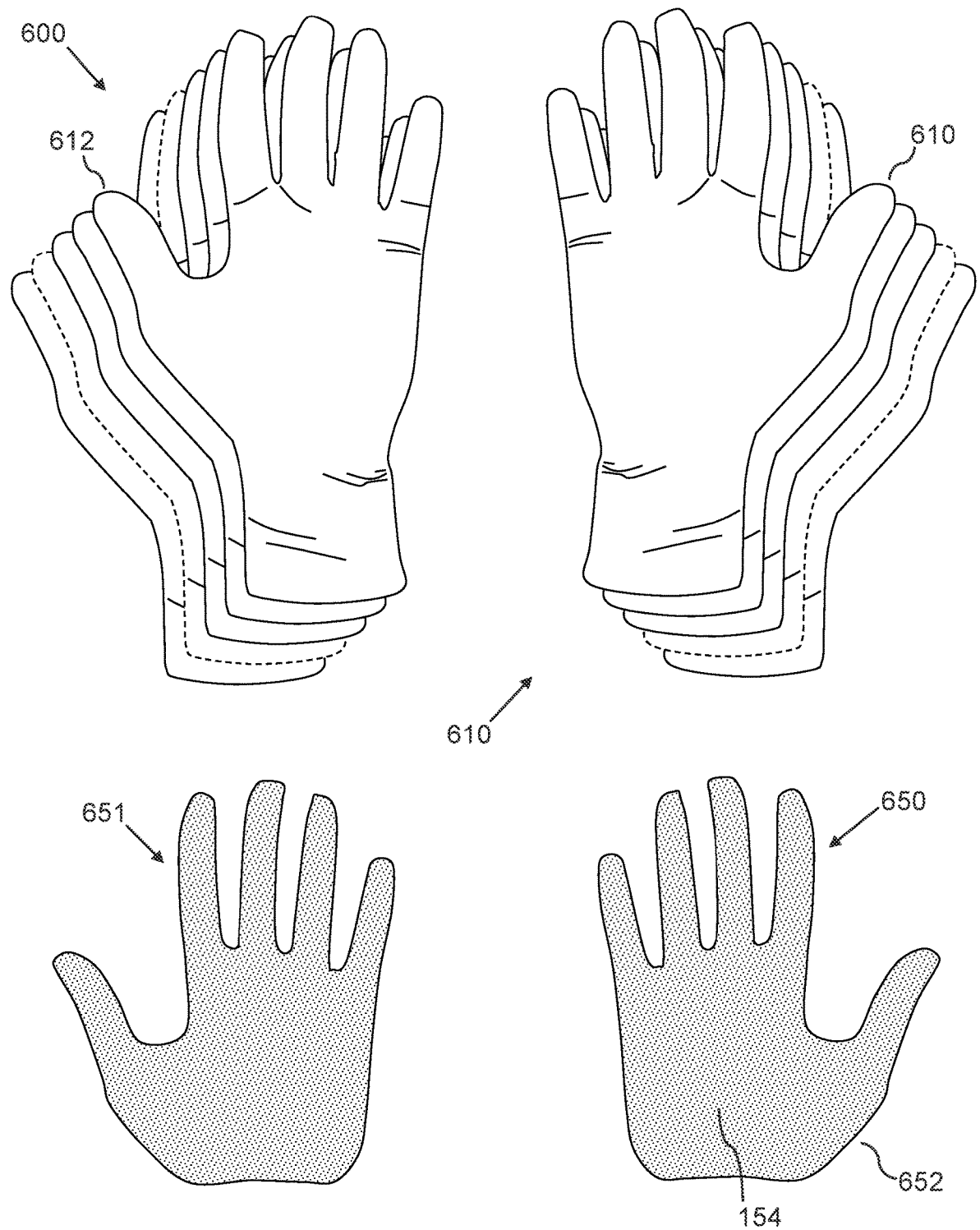
FIG. 6 is a perspective view of a disinfecting glove system, according to an embodiment of the invention.

In a related embodiment, as shown in FIG. 6, a disinfecting glove system 600 can include:

a) a plurality 610 of pairs of right and left disposable glove bodies 610, 612, which are each configured for one-time use, such that each disposable glove body 612, 610 can be configured with a palmar material thickness in a range of less than 10 mil, such as 4-8 mil, but in some cases less than 2 mil; and b) at least one pair of reusable disinfecting pads 650, 651, wherein each reusable disinfecting pad 650, 651 can include:
   i. a pad body 652, which further includes the disinfecting agent 154; and
   ii. an adhesive layer 158, which is positioned on a portion of a palmar side of the pad body;

wherein each reusable disinfecting pad 650, 651 can be configured for reuse, such that the reusable disinfecting pad 650, 651 can for example be cleaned between use, with reapplication of the disinfecting agent 154;

such that the adhesive layer 158 is configured to enable the disinfecting pad 150 to be detachably positionable on a palmar side of the disposable glove body 110, such that the adhesive layer 158 is between the pad body 652 and the at least one glove body 610;

such that each reusable disinfecting pad 650, 651 can be reused over a prolonged period, with sequential attachment, use, and subsequent detachment of each disposable glove body 610, 612.

In related usage, the disinfecting glove system 500 can for example be configured with at least one glove body 110 that are made of a relatively thin rubber, such as a nitrile rubber of no more than 10 mil palmar thickness, for one time use, such as for medical examination, such that the disinfecting pads 150 can be configured to be one-time or limited-usage disposable disinfecting pads 150.

In related embodiments, the disinfecting glove 100:

a) can be configured with a slip fit (finger slides) such that fingers of the disinfecting glove 100 can include an integrated finger sleeve; and/or b) can include an elastic fabric strap to put tension on glove body 110 in order to keep disinfecting pad 150 in place.

In related embodiments, the disinfecting glove 100 can be configured:

a) such that glove body 110 extends to forearm with extended fabric overlay coverage, for the purpose of maximizing the disinfecting surface in fewer wipes. This saves time and speeds up the cleaning process;

b) such that glove body 110 extends to elbow with extended fabric overlay coverage—for the purpose of maximizing the disinfecting surface in fewer wipes. This saves time and speeds up the cleaning process;

c) as a travel pack, such that the disinfecting pad 150 can be dry or pre-saturated with disinfecting solution;

d) such that the disinfecting pad 150 can include a fabric used for dusting (dry fabric vs. pre-soaked fabric);
e) such that the disinfecting pad 150 can include a material used for scrubbing surfaces (such as a SCOTCH BRITE™ scrubbing surface);
f) as disposable disinfecting booties with a disinfecting pad 150 on the sole for the purpose of disinfecting floors.

Figure 7A:
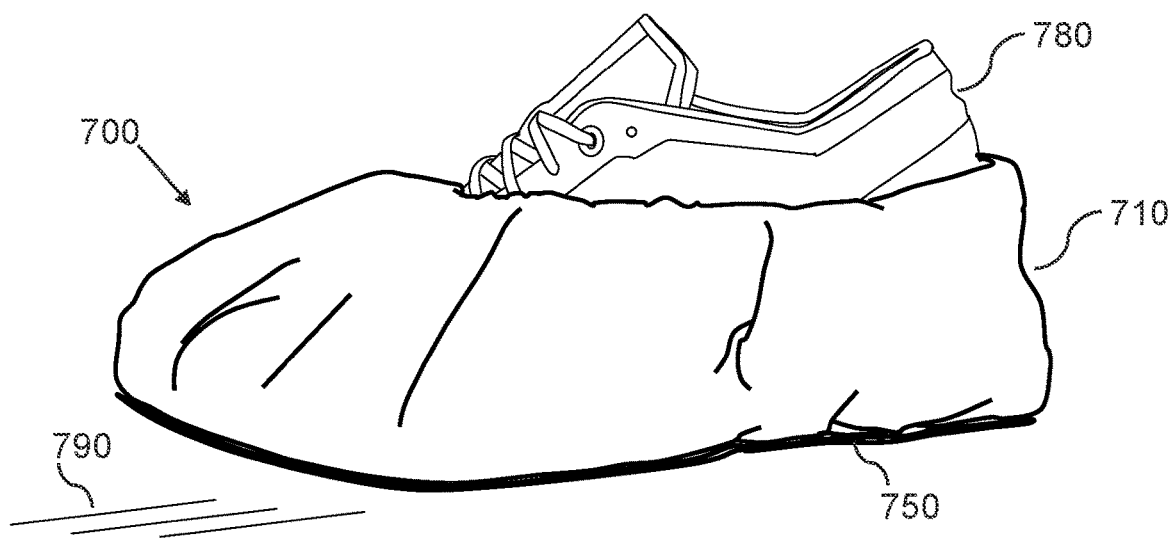
FIG. 7A is a perspective view of a disinfecting shoe cover, which is mounted on a shoe, according to an embodiment of the invention.
Figure 7B:
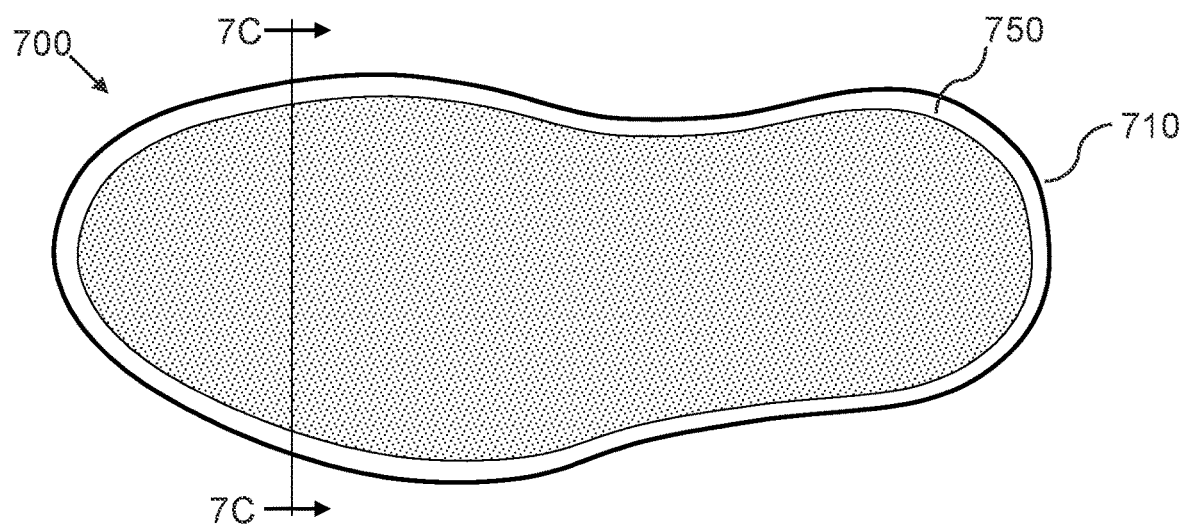
FIG. 7B is a bottom view of a disinfecting shoe cover, according to an embodiment of the invention.
Figure 7C:
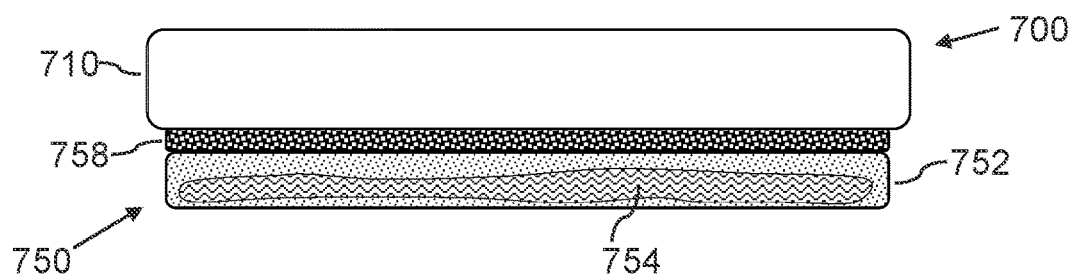
FIG. 7C is a schematic cross-sectional view of a disinfecting shoe cover taken along section line 7C-7C of FIG. 7B, according to an embodiment of the invention.

In an embodiment, as shown in FIGS. 7A, 7B, and 7C, a disposable disinfecting shoe cover 700 can include:
a) a shoe cover body 710, which can be made of rubber, including nitrile rubber, or latex, such that the shoe cover body 710 is configured to be worn on a shoe 780 or foot of a user 180; and
b) a disinfecting pad 750, which can be configured to be detachably positioned on a bottom side (i.e. a sole side) of the shoe cover body 710, wherein the disinfecting pad 150 can further include (i.e. be saturated with):
  i. a disinfecting agent 154;
such that the disposable disinfecting shoe cover 700 can be used to clean a surface 790, such that the disinfecting pad 750 wipes the surface and applies the disinfecting agent to the surface.

Figure 8:
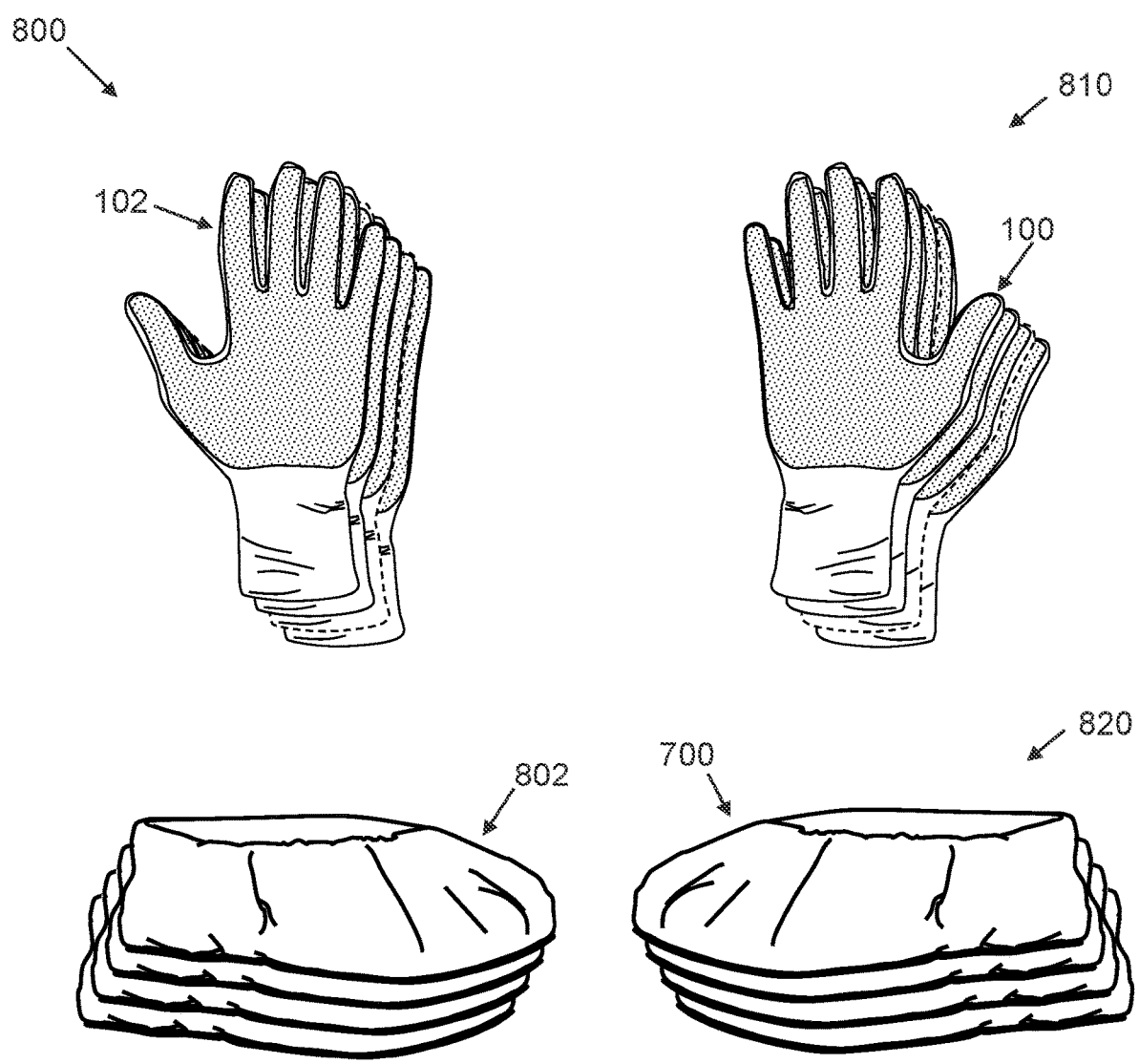
FIG. 8 is a perspective view of a disinfecting system, according to an embodiment of the invention.

In a related embodiment, as shown in FIG. 8, a disinfecting system 800, can include:
a) a plurality 810 of pairs of right and left disinfecting gloves 100, 102; and
b) a plurality 820 of pairs of right and left disinfecting shoe covers 700, 802.

In a related embodiment, as shown in FIGS. 7B and 7C, the disinfecting pad 750 can include:
a) a pad body 752, which further comprises the disinfecting agent 754; and
b) an adhesive layer 758, which can be positioned on an inner side of the pad body 752;
such that the adhesive layer 758 cab be configured to attach the disinfecting pad 750 to the bottom side of the shoe cover body 710, such that the adhesive layer 758 is between the pad body 752 and the shoe cover body 710.

In a further related embodiment, the adhesive layer 758 can be made of a permanent adhesive, such that the pad body 752 is permanently attached to the shoe cover body 752.

In another further related embodiment, the adhesive layer 758 can be made of a pressure sensitive adhesive, such that the pad body 752 is detachably attached to the shoe cover body.

In related embodiments, the disinfecting glove 100, the disinfecting shoe cover 700, the disinfecting glove systems 400, 500, 600, and the disinfecting system 800 can be used in various industries, including:
a) Automotive (Dealer prep and disinfection services);
b) Computer manufacturing and services;
c) Hospitality including: Hotels (House Cleaning, Restaurants, Pool services, etc.);
d) Gyms, to provide equipment disinfecting via gym provided gloves or for use by disinfection/cleaning employee for client safety (a service the client could potentially pay for through slightly increased member fees);
e) Grocery stores, to enhances store cleanliness, including for:
  i. Stocking shelves (Disinfecting cans, bottles and products in general during shelf stocking and restocking)
f) Hospitals, including for:
  i. Neonatal gloves, wherein soft fabric exterior of gloves create a better care experience for newborns (warm fabric vs. rubber gloves);
  ii. Assisted living facilities—fabric allows for personalized care with skin contact, such as for assisting with patients that suffer from bed sores or perpetual wounds/infections;
g) Cleanrooms;
h) Restaurants, such that rapid table and chair disinfecting allowing quicker turnover per table increasing revenue; and
i) Airlines—Rapid seat and tray disinfecting again decreasing time between gate arrival and departure increasing airline revenue.

In related embodiments, the disinfecting glove 100, the disinfecting shoe cover 700, the disinfecting glove systems 400, 500, 600, and the disinfecting system 800 can have a substantial community impact, such as for example related to:
a) Employment creation, herein for example:
  i. In relation to establishing partnerships with rehab centers (Parolees, retirees, disabled employment (wheelchair, hearing impaired, etc.)) and women's shelters to employ gym assistants to clean equipment after each member's use, guaranteeing a disinfected environment (at a premium cost to members); and
  ii. Similar programs with sports venues, music venues, convention centers, VA facilities, etc.

In another related embodiment, to add comfort, ease and reusable functionality, the pad body 152 can be configured as a thin sponge covering the palmer side of the glove body 110, such that each finger's surface area can be separately covered by the sponge. This version will not have quaternary ammonium compounds with sodium hypochlorite added in the packaging. The consumer will have the ability to add the cleaning and disinfecting solution of their choice to the glove when they are ready to use them. They can be cleaned and reused. This will allow for full dexterity and flexibility of fingers while using the glove.

In various related embodiments, the glove 100 can make disinfecting objects while handling them a much easier process and more natural to control; almost as if the hands themselves are disinfecting the object, rather than awkwardly maneuvering an external tool around a product, while attempting to disinfect the entire external surface area of the product. The glove's 100 disposable nature also provides enhanced usability as consumers can easily remove a soiled pair of gloves 100 and apply a fresh pair of gloves 100 as needed. The glove 100 can be used until the pad body 152 is sufficiently soiled, and then disposed of afterward. The gloves 100 can created with both the left hand and right-hand palmar sides covered with the pad body 152. Additional pairs of gloves 100 can be applied as needed, until exterior of a contaminated package has been completely covered with the disinfecting solution.

Here has thus been described a multitude of embodiments of the disinfecting glove 100, the disinfecting shoe cover 700, the disinfecting glove systems 400, 500, 600, and the disinfecting system 800, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A disinfecting glove system, comprising:
    a disinfecting glove, comprising:
        a glove body; and
        a disinfecting pad, which is positioned on a palmar side of the glove body, wherein the disinfecting pad is configured to receive a disinfecting agent, wherein the disinfecting pad comprises:
            a pad body, which comprises:
                a scrubbing portion, which is configured as a scouring pad; and
                a cleaning portion, which is configured as a cleaning cloth, which is less abrasive than the scrubbing portion;
            an adhesive layer, which is positioned on an inner side of the pad body; and
            dusting portions, which are positioned in finger areas of the palmar side of the disinfecting glove;
            such that the adhesive layer is configured to attach the disinfecting pad to the palmar side of the glove body, such that the adhesive layer is between the pad body and the glove body;
    wherein the scrubbing portion is positioned in a lower palm area of the palmar side of the disinfecting glove;
    wherein the cleaning portion is positioned in a central palm area of the palmar side of the disinfecting glove; and
    wherein the scrubbing portion and the cleaning portion are configured to be saturated with the disinfecting agent, for scrubbing and sanitation of a surface;
    such that the dusting portions are used for final dusting of the surface;
    such that the disinfecting glove is configured to clean the surface, such that the disinfecting pad is configured to wipe the surface and apply the disinfecting agent to the surface.

2. The disinfecting glove system of claim 1, wherein the glove body is made of nitrile rubber.

3. The disinfecting glove system of claim 1, wherein the disinfecting pad further comprises:
    the disinfecting agent.

4. The disinfecting glove system of claim 1, wherein the disinfecting agent comprises a quaternary ammonium compound.

5. The disinfecting glove system of claim 1, wherein the adhesive layer is made of a permanent adhesive, such that the pad body is permanently attached to the glove body.

6. The disinfecting glove system of claim 5, wherein the permanent adhesive is cyanoacrylate.

7. The disinfecting glove system of claim 1, wherein the adhesive layer is made of a pressure sensitive adhesive, such that the pad body is detachably attached to the glove body.

8. The disinfecting glove system of claim 7, wherein the pressure sensitive adhesive is a silicone gel.

9. The disinfecting glove system of claim 1, wherein the pad body is made from at least one of:
    a) a polypropylene fabric;
    b) a microfiber fabric;
    c) a cotton fabric; and
    d) combinations thereof.

10. The disinfecting glove system of claim 1, further comprising:
    a glove container;
    wherein the disinfecting glove is packaged and sealed inside the glove container, such that the disinfecting pad of the disinfecting glove remains saturated with disinfecting agent, as long as the glove container remains sealed with the disinfecting glove inside.

* * * * *